(12) United States Patent
Choi et al.

(10) Patent No.: US 10,772,493 B2
(45) Date of Patent: Sep. 15, 2020

(54) DENTAL RETRACTOR

(71) Applicant: DIO Corporation, Busan (KR)

(72) Inventors: Byung Ho Choi, Wonju-si (KR); Seung Mi Jung, Wonju-si (KR); Jin Chul Kim, Yangsan-si (KR); Jin Baek Kim, Busan (KR)

(73) Assignee: DIO CORPORATION, Busan (KR)

( * ) Notice: Subject to any disclaimer, the term of this patent is extended or adjusted under 35 U.S.C. 154(b) by 0 days.

(21) Appl. No.: 15/563,727

(22) PCT Filed: Apr. 4, 2017

(86) PCT No.: PCT/KR2017/003675
§ 371 (c)(1),
(2) Date: Oct. 2, 2017

(87) PCT Pub. No.: WO2018/074683
PCT Pub. Date: Apr. 26, 2018

(65) Prior Publication Data
US 2019/0059714 A1     Feb. 28, 2019

(30) Foreign Application Priority Data

Oct. 20, 2016   (KR) .................. 10-2016-0136328
Dec. 13, 2016   (KR) .................. 10-2016-0169193
Feb. 8, 2017    (KR) .................. 10-2017-0017267

(51) Int. Cl.
*A61B 13/00*     (2006.01)
*A61B 5/00*      (2006.01)
(Continued)

(52) U.S. Cl.
CPC .............. *A61B 1/24* (2013.01); *A61B 5/4547* (2013.01); *A61B 13/00* (2013.01); *A61C 1/08* (2013.01);
(Continued)

(58) Field of Classification Search
CPC ......... A61B 1/24; A61B 5/4547; A61B 13/00; A61B 1/32; A61C 1/08; A61C 3/00;
(Continued)

(56) References Cited

U.S. PATENT DOCUMENTS 3,690,004 A *  9/1972  Frush .................. A61C 9/0006
                                              433/37
4,003,132 A *  1/1977  Beck ................... A61C 9/0006
                                              433/42

(Continued)

FOREIGN PATENT DOCUMENTS

WO   WO 2015/149127    * 10/2015

*Primary Examiner* — Jessica Weiss
(74) *Attorney, Agent, or Firm* — Paratus Law Group, PLLC

(57) ABSTRACT

To accurately acquire an image of an inside of an oral cavity of a person to be treated, there is provided a dental retractor including a retracting base portion that includes an inner retracting portion extending in an arch-shaped profile to surround an inner portion of gum at any one side of an upper jaw and a lower jaw inside an oral cavity and having a pressing holding portion formed at an outer peripheral surface so that a tongue is accommodated therein and an outer retracting portion integrally extending from both ends of the inner retracting portion and extending in an arch-shaped profile to surround an outer portion of the gum, and a handle portion including a grip portion connected outward from the retracting base portion.

6 Claims, 6 Drawing Sheets

(51) Int. Cl.
*A61B 1/24* (2006.01)
*A61C 3/00* (2006.01)
*A61B 1/32* (2006.01)
*A61C 19/04* (2006.01)
*A61C 9/00* (2006.01)
*A61C 1/08* (2006.01)
*A61C 8/00* (2006.01)

(52) U.S. Cl.
CPC ............... *A61C 3/00* (2013.01); *A61C 8/00* (2013.01); *A61C 9/00* (2013.01); *A61C 9/004* (2013.01); *A61C 9/0033* (2013.01); *A61C 19/04* (2013.01); *A61B 1/32* (2013.01)

(58) Field of Classification Search
CPC .......... A61C 8/00; A61C 9/00; A61C 9/0033; A61C 9/004; A61C 19/04
USPC ......................................... 600/239–242, 235
See application file for complete search history.

(56) References Cited

U.S. PATENT DOCUMENTS

| | | | | |
|---|---|---|---|---|
| 4,259,074 A * | 3/1981 | Link | ................... | A61C 13/00 433/214 |
| 4,459,107 A * | 7/1984 | Weissman | ............ | A61C 9/0006 433/213 |
| 4,484,890 A * | 11/1984 | Jouvin | ................... | A61C 9/0006 433/37 |
| 5,135,392 A * | 8/1992 | Polansky | ............ | A61C 9/0006 433/214 |
| 5,199,872 A * | 4/1993 | Leal | ................... | A61B 1/24 433/136 |
| 5,478,235 A * | 12/1995 | Schuldt | ................ | A61C 9/0006 433/37 |
| 5,513,986 A * | 5/1996 | Feltham | ................ | A61C 17/08 433/91 |
| 5,636,985 A * | 6/1997 | Simmen | ................ | A61C 9/0006 433/37 |
| 5,702,250 A * | 12/1997 | Kipke | ................... | A61C 9/0006 433/29 |
| 6,394,802 B1 * | 5/2002 | Hahn | ................... | A61C 9/0006 433/37 |
| 6,629,841 B1 * | 10/2003 | Skinner | ................ | A61C 9/0006 433/43 |
| 6,676,408 B1 * | 1/2004 | Bushnell | ............ | A61C 9/0006 222/638 |
| 6,976,841 B1 * | 12/2005 | Osterwalder | ........ | A61C 9/0006 433/29 |
| 8,376,738 B2 * | 2/2013 | Wagner | ................ | A61C 9/0006 433/6 |
| 2001/0038993 A1 * | 11/2001 | Lindquist | ............ | A61C 9/0006 433/37 |
| 2003/0044748 A1 * | 3/2003 | Tucker | ................ | A61C 9/0006 433/38 |
| 2004/0009451 A1 * | 1/2004 | Skinner | ................ | A61C 9/0006 433/43 |
| 2004/0096801 A1 * | 5/2004 | Tucker | ................ | A61C 9/0006 433/38 |
| 2004/0241606 A1 * | 12/2004 | Diesso | ................... | A61C 9/00 433/37 |
| 2005/0202363 A1 * | 9/2005 | Osterwalder | ........ | A61C 9/0006 433/29 |
| 2006/0068357 A1 * | 3/2006 | Paradiso | ............. | A61C 9/0006 433/39 |
| 2006/0088799 A1 * | 4/2006 | Dorfman | ............. | A61C 9/0006 433/38 |
| 2006/0141416 A1 * | 6/2006 | Knutson | ............. | A61C 9/0006 433/37 |
| 2007/0166659 A1 * | 7/2007 | Haase | ................... | A61C 9/0006 433/37 |
| 2007/0231773 A1 * | 10/2007 | Pontynen | ............... | A61C 17/04 433/140 |
| 2007/0292819 A1 * | 12/2007 | Scarberry | ............... | A61F 5/566 433/140 |
| 2009/0081604 A1 * | 3/2009 | Fisher | ................... | A61C 9/0006 433/24 |
| 2009/0081611 A1 * | 3/2009 | Hines | ....................... | A61B 6/14 433/140 |
| 2009/0177192 A1 * | 7/2009 | Rioux | ................ | A61B 18/1492 606/33 |
| 2009/0239190 A1 * | 9/2009 | Darnell | ................ | A61C 9/0006 433/48 |
| 2010/0019170 A1 * | 1/2010 | Hart | ........................ | A61C 5/90 250/459.1 |
| 2010/0075273 A1 * | 3/2010 | Karlsson | ............... | A61C 9/0006 433/44 |
| 2010/0311008 A1 * | 12/2010 | Gellerfors | ............... | A61F 5/566 433/93 |
| 2012/0219925 A1 * | 8/2012 | Tropmann | ........... | A61C 9/0006 433/37 |
| 2012/0231932 A1 * | 9/2012 | Rafih | ................... | A63B 71/085 482/11 |
| 2013/0230822 A1 * | 9/2013 | Hines | ...................... | A61B 1/32 433/29 |
| 2016/0022381 A1 * | 1/2016 | Jessop | ..................... | A61B 1/32 433/140 |
| 2017/0020716 A1 * | 1/2017 | Hart | ........................ | A61F 5/566 |
| 2018/0014962 A1 * | 1/2018 | Lee | ........................ | A61F 5/058 |

* cited by examiner

【Fig. 1】
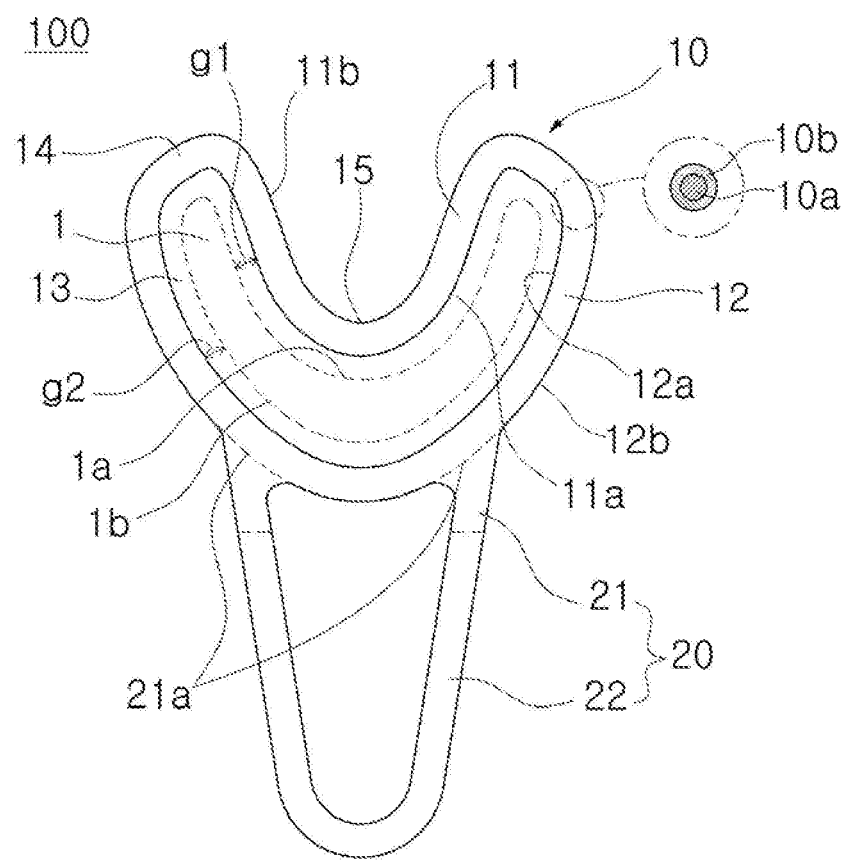
【Fig. 2】
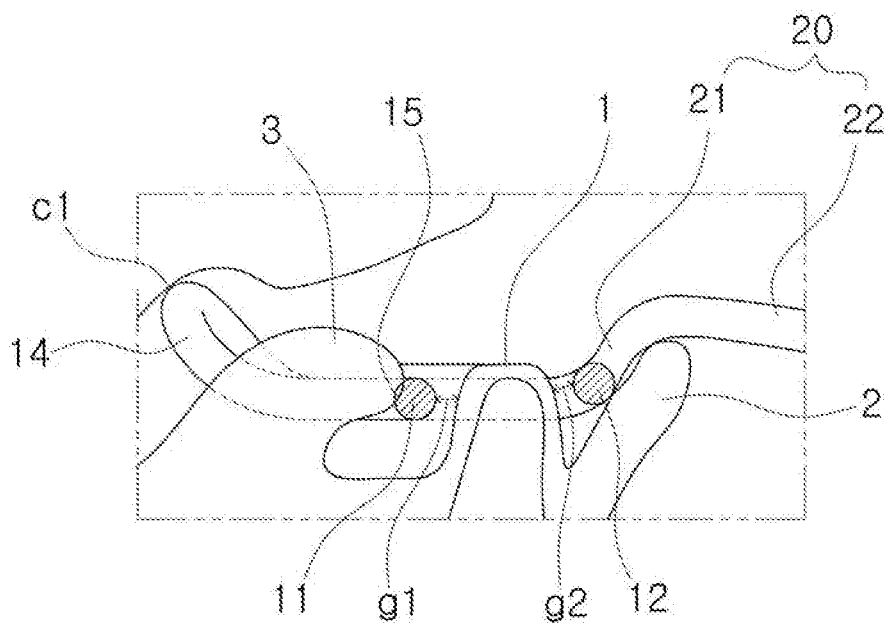

[Fig. 3]
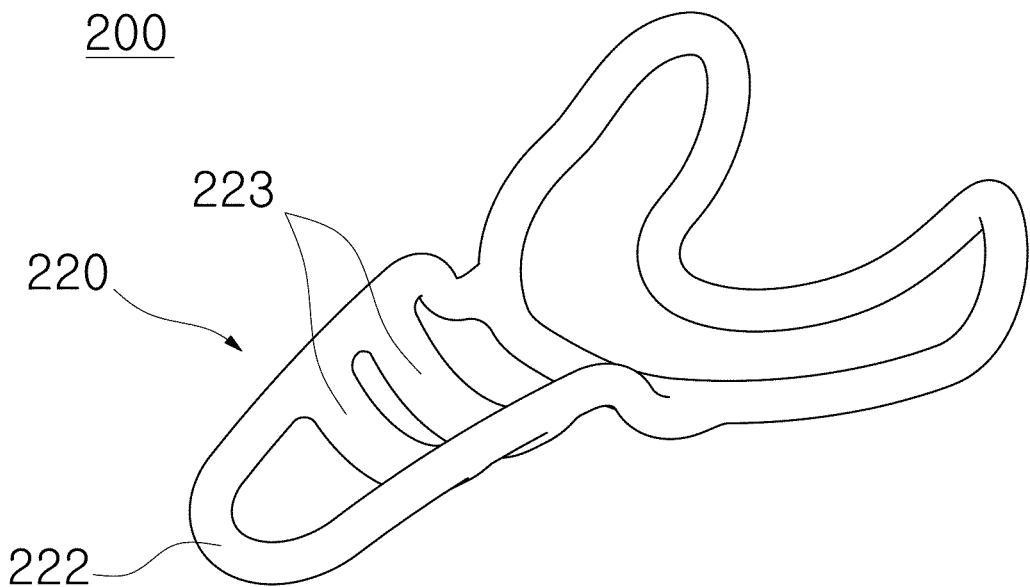
[Fig. 4]
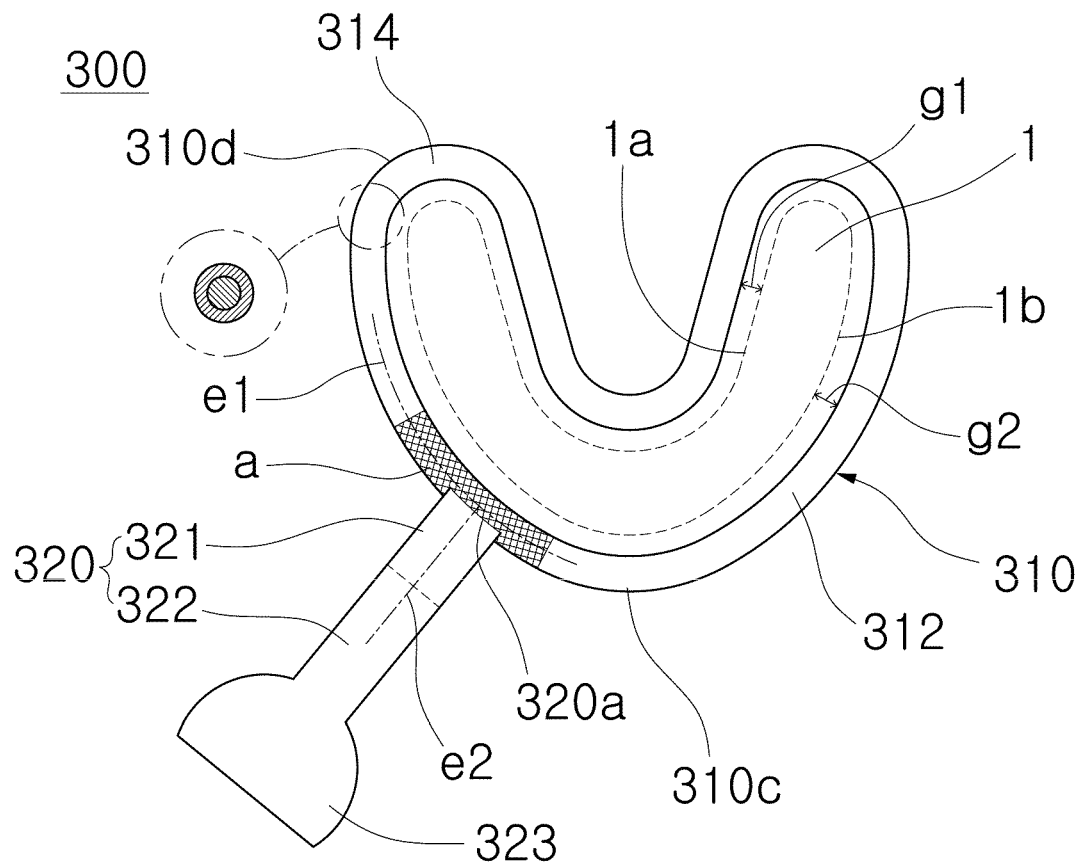

[Fig. 5]
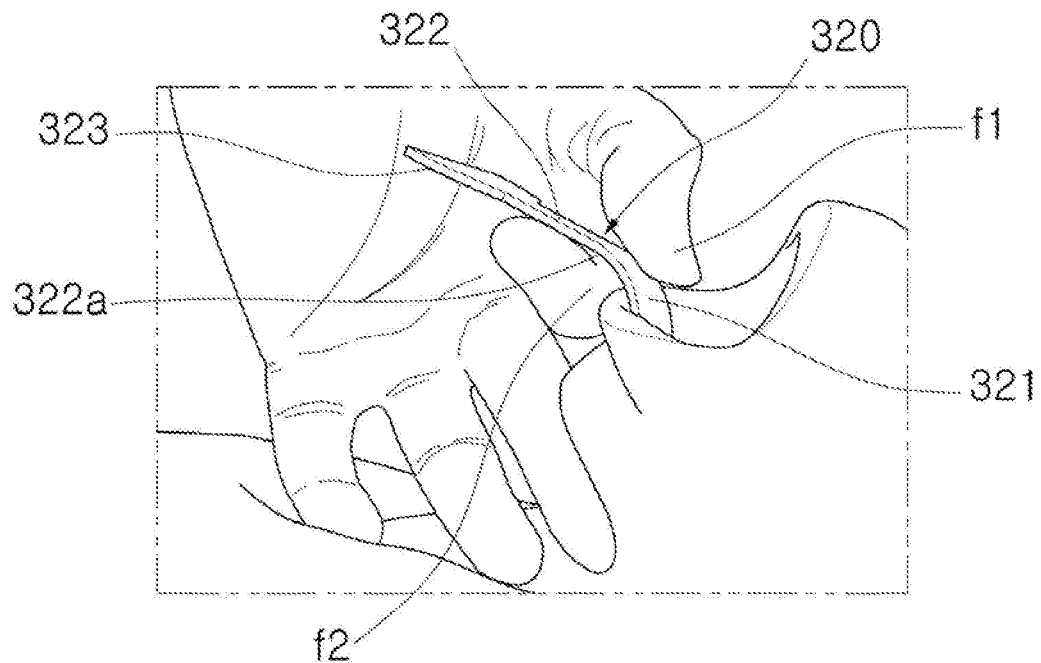
[Fig. 6]
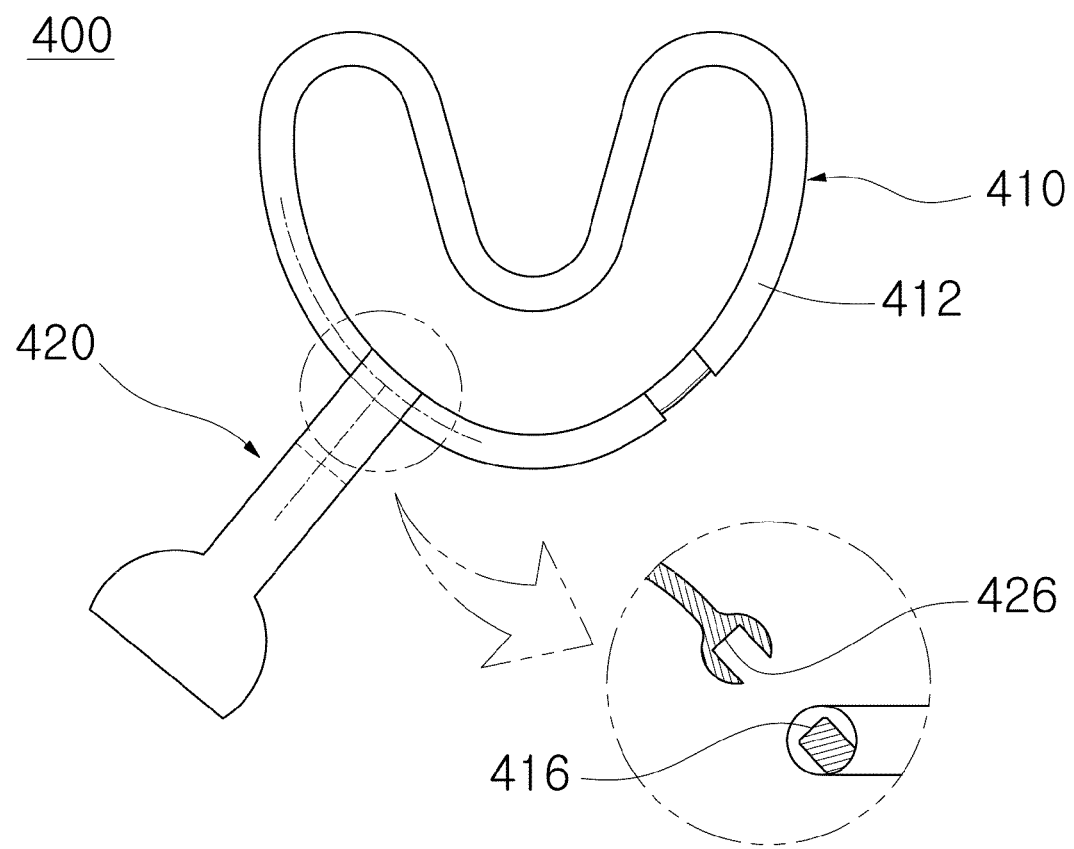

[Fig. 7]
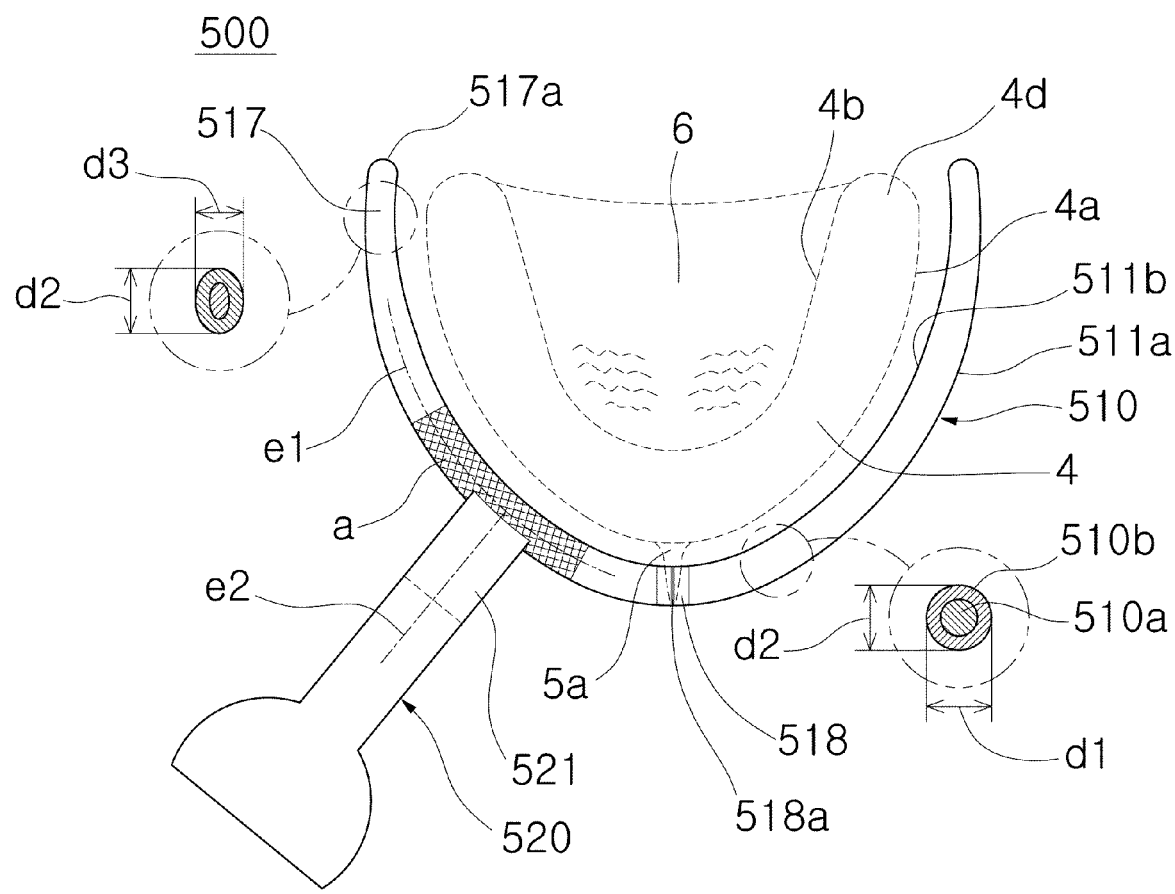
[Fig. 8]
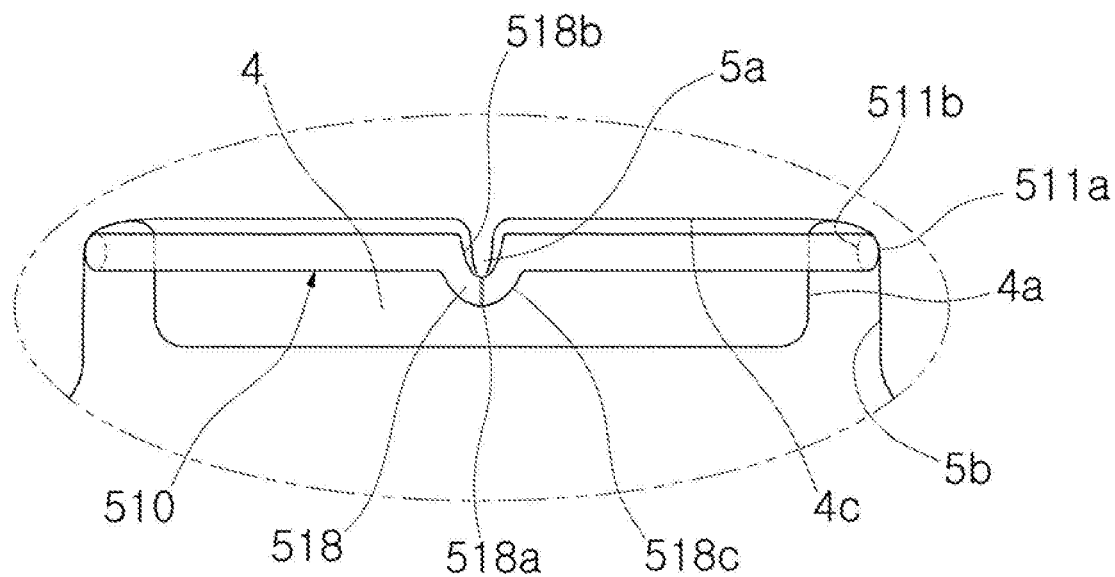

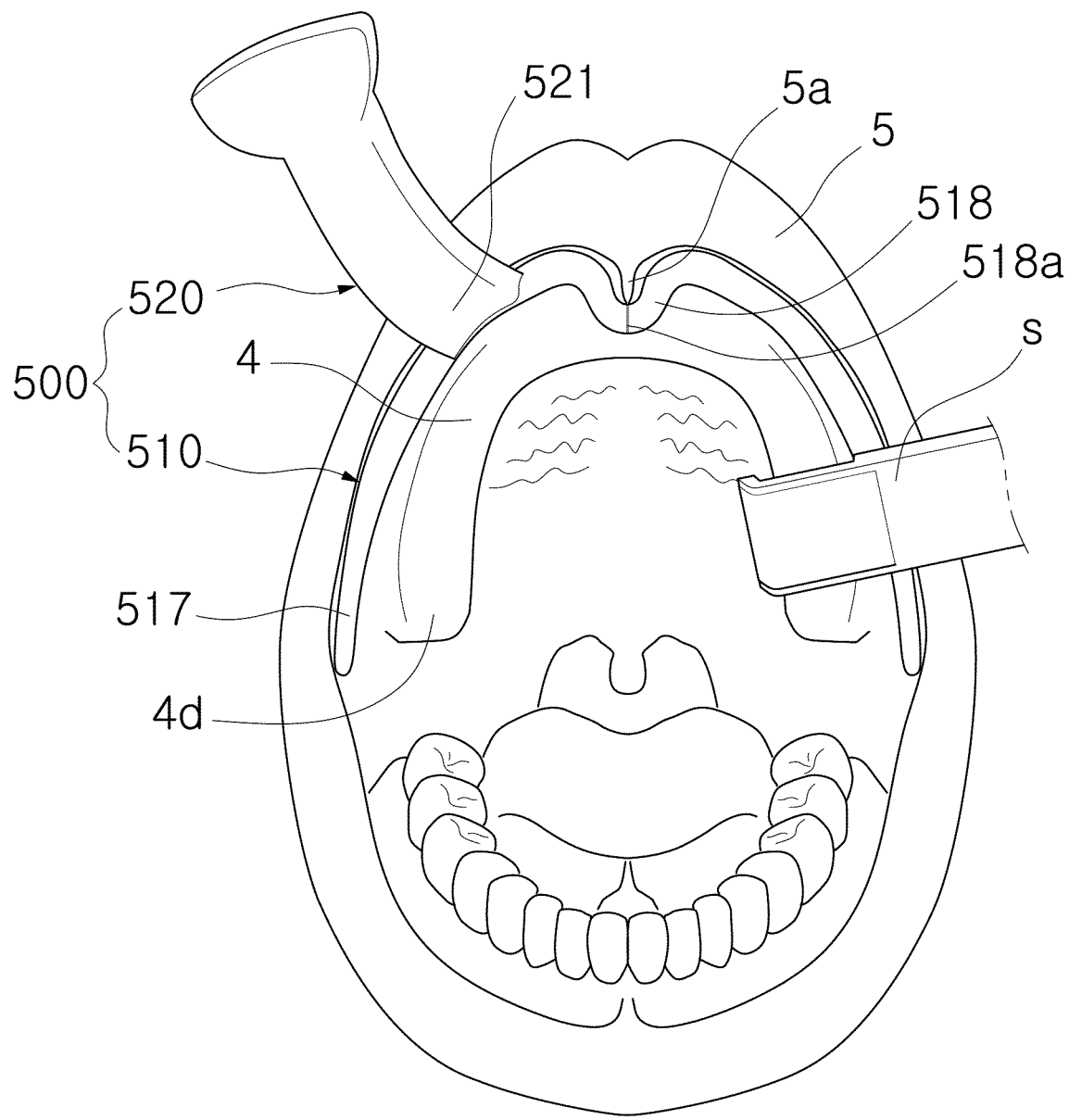
[Fig. 9]

[Fig. 10]
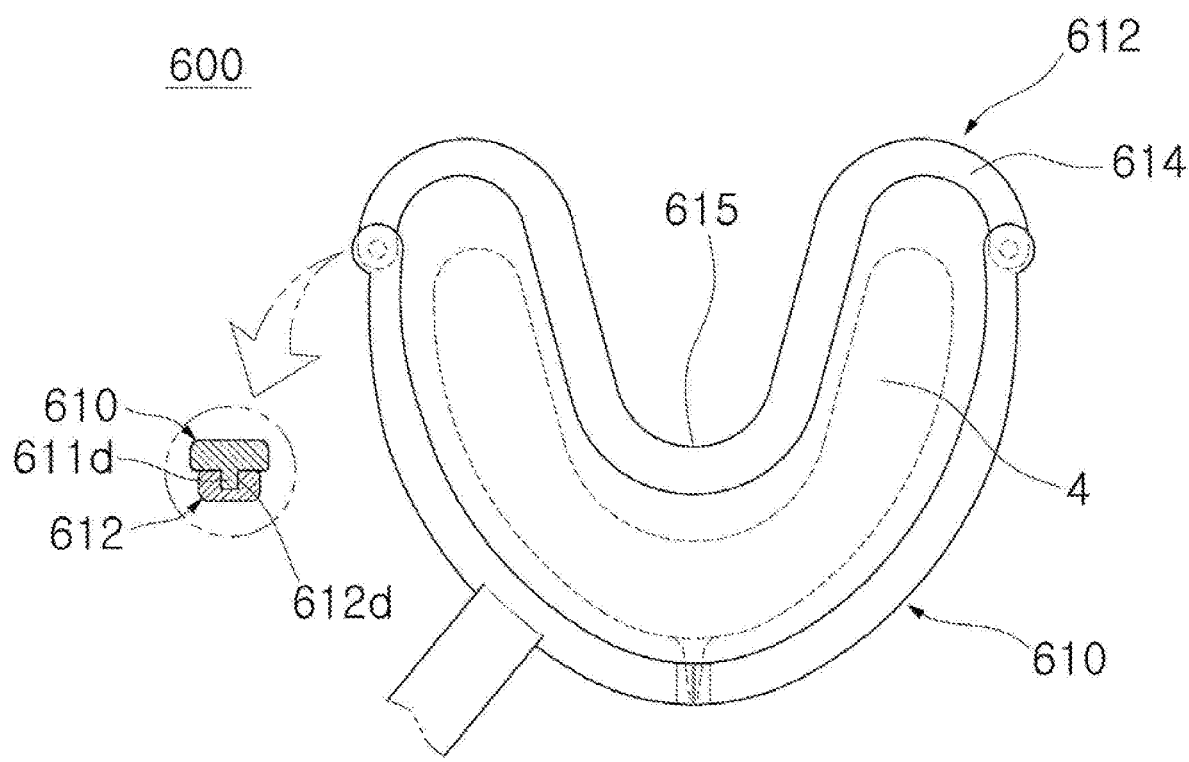

DENTAL RETRACTOR

CROSS REFERENCE TO PRIOR APPLICATIONS

This application is a National Stage Patent Application of PCT International Patent Application No. PCT/KR2017/003675 (filed on Apr. 4, 2017) under 35 U.S.C. §371, which claims priority to Korean Patent Application Nos. 10-2016-0136328 (filed on Oct. 20, 2016), 10-2016-0169193 (filed on Dec. 13, 2016), and 10-2017-0017267 (filed on Feb. 8, 2017), which are all hereby incorporated by reference in their entirety.

TECHNICAL FIELD

The present invention relates to a dental retractor, and more particularly, to a dental retractor for accurately acquiring an image of an oral cavity of a person to be treated.

BACKGROUND ART

An implant generally refers to a substitute that can substitute for a human tissue when an original human tissue is lost but refers to implanting an artificially made tooth in dentistry.

To place an implant, first, a perforation is formed in an alveolar bone using a drill and a fixture is placed in the perforation. The perforation formation and the implant placement are differently performed for each person to be treated. This is because a position, a depth, and a direction of an implant placement should be determined in consideration of various factors such as a state of a tooth of a person to be treated, a position of a tooth that requires an implant placement, a state of an alveolar bone of the person to be treated, or the like.

In this way, it is very difficult for an experienced person as well as an inexperienced unskilled person to accurately determine the depth and the direction in a drilling task for forming a perforation in an alveolar bone. Further, it is extremely difficult for an unskilled person to determine a depth of a perforation formed during drilling without a separate measurement step. Accordingly, an auxiliary tool referred to as a surgical guide is used to guide an accurate depth, position, and direction of a perforation.

A conventional surgical guide is manufactured through the following process. First, a 3D image of an inside of an oral cavity of a person to be treated is acquired by computerized tomography (CT) scanning, and a 3D exterior image of the inside of the oral cavity of the person to be treated is acquired through oral scan. Here, information related to a crown, a dental root inside the oral cavity, and a shape and bone density of an alveolar bone is included in the 3D image. Exterior information related to shapes of a crown and gum inside the oral cavity is included in the 3D exterior image.

When each of the images is acquired, the two images are matched on the basis of a set point inside the oral cavity such as abnormality of a tooth. Then, an implant placement plan is established through a matched result, and the surgical guide is manufactured according to the placement plan.

Here, the 3D exterior image is acquired by directly scanning the inside of the oral cavity of the person to be treated using an oral scanner, and there is a problem in that it is difficult to accurately acquire an image due to movement of soft tissues such as the tongue, the lips, and inner surfaces of cheeks.

That is, because an accurate scanning task is difficult due to movement of the tongue interfering with a scanning path of the oral scanner, a step of performing a correcting task for an acquired 3D exterior image is required, and time is required for the correcting task, there are problems in that an implant placement period increases and economic feasibility decreases. Also, it is difficult for an operator to accurately check an inside of an oral cavity of a person to be treated due to the person to be treated unconsciously moving his or her lips, a space and a path through which the oral scanner is moved are not sufficiently secured, and accuracy of an acquired image decreases.

Furthermore, because a soft tissue such as buccal mucosa substantially surrounds and is adhered to an outer portion of gum, it is difficult for the oral scanner to be inserted thereinto, and an unnecessary image of soft tissues is included in the 3D exterior image. Consequently, it is difficult to utilize the 3D exterior image as data for image matching when an outer shape of the soft tissue is included in the 3D exterior image, and there is a problem of causing an inconvenience to a person to be treated due to repeated oral scans.

Further, because a retracting tool capable of holding each of the soft tissues to prevent movement of the tongue and the lips is separately disposed, there are problems in that it is difficult for an operator to operate and the scanning task efficiency decreases due to requiring an assistant operator.

The 3D exterior image can be acquired when manufacturing dentures of a person to be treated who is edentulous or partially edentulous as well as when placing an implant.

Specifically, a fixing groove portion formed inside an oral cavity so that a denture is fitted thereto is designed on the basis of an outer profile of gum included in the 3D exterior image. Here, there is a problem in that design precision of the fixing groove portion decreases when the outer shape of the soft tissue is included in the 3D exterior image. Thus, there are problems in that reliability of masticatory efficiency decreases due to a manufactured denture being unable to be accurately installed inside an oral cavity of a person to be treated, and an inconvenience of the person to be treated increases due to pain in the gum during occlusion.

DISCLOSURE

Technical Problem

To solve the above problems, the present invention is directed to providing a dental retractor for accurately acquiring an image of an inside of an oral cavity of a person to be treated.

Technical Solution

To solve the above objective, there is provided a dental retractor including a retracting base portion that includes an inner retracting portion extending in an arch-shaped profile to surround an inner portion of gum at any one side of an upper jaw and a lower jaw inside an oral cavity and having a pressing holding portion formed at an outer peripheral surface so that a tongue is accommodated therein and an outer retracting portion integrally extending from both ends of the inner retracting portion and extending in an arch-shaped profile to surround an outer portion of the gum, and a handle portion including a grip portion connected outward from the retracting base portion.

Further, there is provided a dental retractor including a retracting base portion inserted between an outer portion of gum and an inner surface of lips so that soft tissues inside an oral cavity are retracted and held outward and an entire outer surface of the gum is exposed and extending in an arch-shaped profile corresponding to the outer portion of the gum, and a handle portion extending outward in a radial direction from a connecting region spaced apart from any one side of both ends with respect to a central portion of the retracting base portion.

Advantageous Effects

A dental retractor of the present invention provides the following advantageous effects.

First, because a tongue is held and retracted by a pressing holding portion formed in an inner retracting portion while lips and inner surfaces of cheeks are pressed and retracted outward at an outer peripheral surface of an outer retracting portion, a state in which the entire gum is exposed can be stably maintained. In this way, because interference due to soft tissues in an oral cavity is minimized during scanning, a reliability of an acquired scanned image can be considerably improved.

Second, because a retracting base portion includes a wire formed of a metal material that is three-dimensionally plastically deformed due to an external force so that the shape of the retracting base portion can be easily adjusted according to individual variations of people to be treated and is covered by an outer skin portion formed of an opaque synthetic resin material, an image defect due to scattering of light during scanning can be prevented.

Third, because a handle portion is eccentric to one side from a central portion of the retracting base portion and extends outward in a diagonal direction to correspond to a natural movement radius of an arm, an excessive bending of a wrist can be prevented when gripping the handle portion, and because a space into which an oral scanner or the like is inserted is maximally secured at a side opposite to the handle portion, convenience of task can be considerably improved.

Fourth, because an alignment reference portion formed at the central portion of the retracting base portion can be disposed at an accurate position by a simple method in which the alignment reference portion is disposed to be aligned to a midline of an inside of an oral cavity, and accurate midline information of a person to be treated is calculated on the basis of alignment reference portion information included in a scanned image, reliability of an implant placement plan can be considerably improved.

DESCRIPTION OF DRAWINGS

FIG. 1 is a plan view of a dental retractor according to a first embodiment of the present invention.

FIG. 2 is an exemplary view illustrating a use state of the dental retractor according to the first embodiment of the present invention.

FIG. 3 is a perspective view illustrating a dental retractor according to a second embodiment of the present invention.

FIG. 4 is a plan view of a dental retractor according to a third embodiment of the present invention.

FIG. 5 is an exemplary view of a state of gripping the dental retractor according to the third embodiment of the present invention.

FIG. 6 is a plan view of a dental retractor according to a fourth embodiment of the present invention.

FIG. 7 is a plan view of a dental retractor according to a fifth embodiment of the present invention.

FIG. 8 is an exemplary view illustrating an inside of an oral cavity in which the dental retractor according to the fifth embodiment of the present invention is installed.

FIG. 9 is an exemplary view illustrating a state in which the inside of the oral cavity in which the dental retractor according to the fifth embodiment of the present invention is installed is scanned.

FIG. 10 is a plan view of a dental retractor according to a sixth embodiment of the present invention.

MODES OF THE INVENTION

FIG. 1 is a plan view of a dental retractor according to a first embodiment of the present invention, and FIG. 2 is an exemplary view illustrating a use state of the dental retractor according to the first embodiment of the present invention. In the drawings, preferably, a dotted line 1 (4 of FIG. 7) within a retracting base portion may be understood as a marking of an entire outer profile of gum. Also, preferably, an outer portion 1a (4a of FIG. 7) of the gum 1 (4 of FIG. 7) may be understood as a portion corresponding to labial and buccal inner surfaces and an inner portion 1b (4b of FIG. 7) of the gum 1 (4 of FIG. 7) may be understood as a portion corresponding to a lingual root or a palate 6 (see FIG. 7).

As illustrated in FIGS. 1 and 2, a dental retractor 100 according to a first embodiment of the present invention includes a retracting base portion 10 and a handle portion 20. Here, preferably, the dental retractor 100 may be understood as a device that has one side disposed inside an oral cavity and is used to hold and retract movement of soft tissues such as the tongue, the lips, and inner surfaces of cheeks to acquire a clear exterior image of gum using an oral scanner.

Specifically, the retracting base portion 10 is disposed to entirely surround the inner portion 1a and the outer portion 1b of the gum 1 of at least one of an upper jaw and a lower jaw inside the oral cavity and preferably includes an inner retracting portion 11 and an outer retracting portion 12.

Here, preferably, the inner retracting portion 11 may extend in an arch-shaped profile to surround the inner portion 1a of the gum 1 and have a pressing holding portion 15 concavely formed at an outer peripheral surface so that a tongue 3 is accommodated therein. Here, preferably, an outer peripheral surface 11b of the inner retracting portion 11 may be understood as an outer surface of a lingual root. Also, the outer retracting portion 12 integrally extends from both ends of the inner retracting portion 11 and is formed in an arch-shaped profile to surround the outer portion 1b of the gum 1.

Here, an accommodating space 13 that entirely surrounds and accommodates the inner portion 1a and the outer portion 1b of the gum 1 is formed between the inner retracting portion 11 and the outer retracting portion 12.

Specifically, preferably, the accommodating space 13 may be set to include a predetermined first interval g1 so that an inner peripheral surface 11a of the inner retracting portion 11 is spaced apart from the inner portion 1a of the gum 1. Also, because the accommodating space 13 is set to include a predetermined second interval g2 so that an inner peripheral surface 12a of the outer retracting portion 12 is spaced apart from the outer portion 1b of the gum 1, the accommodating space 13 may be formed to be substantially larger than the profiles of the inner portion 1a and the outer portion 1b of the gum 1.

Further, the first interval g1 and the second interval g2 may be set to cover individual variations in gum profiles according to gender and age. Consequently, because a single dental retractor can be compatibly used for various people to be treated, economic feasibility and convenience in use can be considerably improved. According to circumstances, the retracting base portion may be manufactured such that a plurality of standardized retracting base portions are manufactured to represent each variation.

Here, when the retracting base portion 10 is inserted into the oral cavity and is disposed so that the gum 1 is accommodated in the accommodating space 13, an outer surface of the tongue 3 is adhered to and held by the pressing holding portion 15 and is retracted toward a distal side inside the oral cavity. Also, because an outer peripheral surface 12b of the outer retracting portion 12 presses and retracts lips 2 and inner surfaces of cheeks outward, the lips 2 and the inner surfaces of the cheeks are spaced apart from the outer portion 1b of the gum 1.

Consequently, a sufficient space in which the oral scanner may be moved can be secured inside the oral cavity, and deviation of the oral scanner from the scanning path due to interference can be prevented even when a person to be treated unconsciously moves his or her lips or tongue. Because the soft tissue is substantially spaced apart from the inner portion 1a and the outer portion 1b of the gum 1, the entire outer shape of the gum 1 is more clearly exposed. In this way, an operator can visually clearly recognize the inside of the oral cavity of the person to be treated and acquire an accurate scanned image using the oral scanner, and reliability of the acquired scanned image can be improved.

Here, when the retracting base portion 10 is disposed inside the oral cavity, the tongue 3 may be retracted toward the distal side of the oral cavity while the lips and the cheeks are pressed and retracted outward from the oral cavity. Therefore, because the soft tissues whose retraction directions are different are entirely spaced apart from the inner portion 1a and the outer portion 1b of the gum 1 using a single tool, convenience of operation can be considerably improved. Further, even in a case in which the amount of gum, which is soft tissue, is large as in a person to be treated who lost most teeth and is edentulous or partially edentulous, because the retracting base portion 10 presses and fixes the gum 1, the outer shape of the gum can be more clearly exposed.

Preferably, the handle portion 20 may extend outward from the retracting base portion 10 and include a grip portion 22. Here, preferably, the grip portion 22 may be connected outward from an extending bent portion 21 and extend in a length that facilitates gripping.

Specifically, preferably, the extending bent portion 21 may be disposed to connect an outer end of the retracting base portion 10 and the grip portion 22 with an upward slope. Here, an outer end of the outer retracting portion 12 is a portion at which the outer retracting portion 12 is convexly round outward and may be preferably understood as a central portion corresponding to a labial side of the oral cavity.

Consequently, the retracting base portion 10 and the grip portion 22 are connected to be substantially stepped. In this way, a pressing force transmitted to the dental retractor 100 may be evenly applied corresponding to a lower end side profile of the gum 1 formed more inward than an upper surface of the lips 2. Here, preferably, the lower end side of the gum may be understood as a connecting portion between the inner portion 1a of the gum 1a and the tongue 3 and a connecting portion between the outer portion 1b of the gum 1 and the lips 2.

Here, the extending bent portion 21 may be disposed as a pair, and the pair of extending bent portions 21 may be spaced a predetermined interval from each other and be symmetrical to each other. Further, the pair of extending bent portions 21 may be connected to left and right canine teeth or first premolar teeth at any one of the upper jaw and the lower jaw. Accordingly, when lower surfaces of the pair of extending bent portions 21 are adhered to the upper surface of the lips 2 while the retracting base portion 10 is inserted into the oral cavity, the retracting base portion 10 is pressed toward a lower end of the gum 1. Then, when the soft tissues are retracted while in contact with the outer peripheral surfaces of the inner retracting portion 11 and the outer retracting portion 12, the inner portion 1a and the outer portion 1b of the gum 1 may be clearly exposed, and a sufficient space in which the oral scanner may be moved can be secured. Further, the lips 2 may be pressed and retracted outward from the oral cavity corresponding to inclined lower surfaces of the pair of extending bent portions 21. Accordingly, because the inner surface of the lips 2 is spaced apart from the outer portion 1b of the gum 1 and movement of the lips 2 is restricted, interference due to the lips 2 may be minimized in the scanning process.

Here, although the extending bent portions 21 may be integrally disposed and connected, the pair of extending bent portions 21 may be spaced apart from each other corresponding to an interval between the left and right canine teeth or the first premolar teeth so that the lips 2 are pressed to be at a uniform interval. Therefore, the anterior teeth side lips as well as the canine teeth and the premolar teeth may be entirely spaced apart from the outer portion 1b of the gum 1, and interference with the oral scanner due to movement of the lips 2 can be prevented. Also, because an unnecessary image of lips is not included in the scanned image, accuracy of the scanned image can be further improved.

Further, the extending bent portions 21 may be inclined upward at a predetermined angle with the outer retracting portion 12 while the grip portion 22 is formed to be inclined downward at a predetermined angle with the extending bent portions 21. Consequently, the outer retracting portion 12 and the grip portion 22 may be disposed in directions substantially corresponding to each other and be formed to be stepped by the extending bent portions 21. In this way, by preventing an opening of the oral cavity from being occluded by the grip portion 22, the scanning path using the oral scanner can be stably secured.

When the operator presses the dental retractor 100 toward the inner surface of the oral cavity while gripping the grip portion 22, the lower surface of the retracting base portion 10 may be adhered to the lower end side of the gum 1 and pressed. Consequently, the tongue 3 is pressed toward the distal side by the inner retracting portion 11, and the lips 2 and the cheeks are pressed outward from the oral cavity by the outer retracting portion 12 while the inner surface of the oral cavity is pressed.

In this way, because the oral scanner is stably moved inside the oral cavity as movements of the soft tissues inside the oral cavity are entirely prevented, the reliability of the scanned image can be considerably improved. Even when a marker (not illustrated) is attached as a reference for image matching at an outer surface of the gum 1, separation due to movement of the soft tissues inside the oral cavity may be prevented. Consequently, accuracy of an implant placement plan can be considerably improved by accurate image matching between a CT image obtained by CT scanning and the scanned image.

Here, outer ends of the outer retracting portion are disconnected corresponding to an interval between the pair of extending bent portions, and ends of the pair of extending bent portions may respectively extend from the disconnected ends of the outer ends of the outer retracting portion. Accordingly, when an interval between opposite sides of the grip portion narrows due to a force of grasping the grip portion integrally extending from the ends of the extending bent portions, an interval between the extending bent portions and an interval between the both disconnected ends of the outer retracting portion may also narrow. Consequently, an interval between the outer portion of the gum and the inner peripheral surface of the outer retracting portion may be elastically adjusted by the grasping force of the operator. Further, the extending bent portions may integrally be bent and extend from the both disconnected ends of the outer retracting portion, and the handle portion and the retracting base portion may be separately disposed such that ends of the extending bent portions are connected to the outer ends of the outer retracting portion.

Preferably, both ends of each of the inner retracting portion 11 and the outer retracting portion 12 may be integrally connected by a connecting portion 14. That is, when it is said that the outer retracting portion 12 integrally extends from both ends of the inner retracting portion 11, preferably, it may be understood that the outer retracting portion 12 and the inner retracting portion 11 are integrally connected by the connecting portion 14. Consequently, preferably, the inner retracting portion 11, the connecting portion 14, and the outer retracting portion 12 may be understood as being formed of substantially a single wire and being distinguished depending on functions thereof.

Specifically, preferably, the connecting portion 14 may be formed to be convexly round corresponding to outer sides of both ends of the retracting base portion 10, preferably, a retromolar trigone profile. The connecting portion 14 may be bent to be inclined upward to face outer surfaces of the extending bent portions 21. Consequently, a state in which an outer portion c1 of the other side gum is seated at the end of the connecting portion 14 that is round outward and the upper and lower jaws are spaced apart may be supported while the lower surface of the retracting base portion 10 may be stably disposed without being interfered by a profile inside the oral cavity. In this way, because the upper and lower jaws of the person to be treated are prevented from being arbitrarily occluded in the process in which the inside of the oral cavity is scanned, the scanning process can be more stably performed, and clarity of the acquired scanned image can be improved.

Preferably, the retracting base portion 10 may include a soft wire portion 10a in which a three-dimensionally plastically deformed shape is maintained due to an external force and an outer skin portion 10b formed of a synthetic resin material and configured to surround an outside of the wire portion 10a.

Specifically, the wire portion 10a is formed corresponding to the arch-shaped profile in which the accommodating space 13 is formed so that the inner retracting portion 11, the outer retracting portion 12, and the connecting portion 14 entirely surrounds the inner portion 1a and the outer portion 1b of the gum 1. Here, the wire portion 10a may be formed of a material that is easy to three-dimensionally deform due to an external force to correspond to individual variations of people to be treated and, once the deformation is completed, is prevented from deformation until an additional external force is applied. For example, the wire portion 10a may be formed of a wire formed of a metal material that can be bent or unfolded due to an external force. Consequently, because the interval between the inner retracting portion 11 and the outer retracting portion 12 or an angle of the connecting portion 14 can be immediately and elastically changed corresponding to various oral environments of people to be treated, usability and economic feasibility can be improved.

An outside of the wire portion 10a may be covered by the outer skin portion 10b. Here, the outer skin portion 10b may be formed of a synthetic resin material such as silicon and polyethylene (PE) that may be elastically deformed together with plastic deformation of the wire portion 10a and may be used in a medical instrument. Preferably, the outer skin portion 10b may be formed of an opaque material by which the wire portion 10a formed of a metal material may be substantially shielded. Consequently, scattering of light due to the wire portion 10a can be prevented during the scanning, and discomfort and resistance of the person to be treated when the wire portion 10a comes into contact with the inside of the oral cavity of the person to be treated can be minimized.

Like the retracting base portion 10, the handle portion 20 may also include an outer skin portion formed of a synthetic resin material configured to cover an outside of a wire portion formed of a metal material. Here, preferably, the wire portion constituting the handle portion 20 may be formed of a stiff material which is substantially not deformed even by a pressing force for retracting the soft tissues. That is, because the retracting base portion 10 is deformable due to an external force and the handle portion 20 has a strength capable of supporting the external force, a retracting force by pressing the soft tissues can be considerably improved.

Here, in a state in which the wire portion at the retracting base portion and the wire portion at the handle portion are formed of separate metal wires having different stiffness and connecting portions thereof are welded to or engaged with each other, the outer skin portion may integrally cover outer surfaces of the wire portions. Alternatively, the retracting base portion and the handle portion may be separately manufactured so that each of the retracting base portion and the handle portion includes a wire portion and an outer skin portion, and connecting portions thereof may be welded, attached and engaged. Further, a plurality of wires formed of the same metal material may overlap in each of the wire portion of the retracting base portion and the wire portion of the handle portion, and strengths of the wire portions may be adjusted by varying a thickness at which the wires overlap.

FIG. 3 is a perspective view illustrating a dental retractor according to a second embodiment of the present invention. In the present embodiment, because fundamental configurations except a handle portion 220 are the same as in the above-described first embodiment, detailed descriptions of overlapping configurations will be omitted.

As illustrated in FIG. 3, a pressing support portion 223 configured to connect opposite sides of a grip portion 222 by a predetermined width so that an operator's fingers are supported when the operator grips the handle portion 220 may be formed. Here, the pressing support portion 223 may be connected in the shape of a concave groove between opposite sides of the grip portion 222 in a direction in which the operator's pressing force is applied.

For example, the handle portion 220 may be gripped in a state in which the operator's thumb is seated on the concave groove of the pressing support portion 223 and the operator's forefinger is supported at a convex outer surface (lower surface) of the pressing support portion 223. When a force is applied in a state in which the handle portion 220 is gripped as above, because a state in which the soft tissues inside the oral cavity are retracted using a dental retractor 200 by the operator is stably maintained, the scanning task can be promptly and accurately performed.

A guide portion configured to guide a scanning path of the oral scanner may be formed in the inner retracting portion. Here, the guide portion may be formed as an arch-shaped groove corresponding to the profile of the inner retracting portion so that an end of the oral scanner is locked and held. That is, when the oral scanner moves along the guide portion, because a distortion between scanned images can be minimized, an image correcting task can be facilitated, and an amount of time required for the task can be shortened.

FIG. 4 is a plan view of a dental retractor according to a third embodiment of the present invention, and FIG. 5 is an exemplary view of a state of gripping the dental retractor according to the third embodiment of the present invention. In the present embodiment, because fundamental configurations except a handle portion 320 are the same as in the above-described first embodiment, detailed descriptions of overlapping configurations will be omitted.

As illustrated in FIGS. 4 and 5, the handle portion 320 may eccentrically extend from a connecting region a (hatching portion) spaced apart from any one side of both ends 310d with respect to a central portion 310c of a retracting base portion 310. Here, the handle portion 320 may include a grip portion 322 stepped upward from the retracting base portion 310.

Here, preferably, the both ends 310d of the retracting base portion 310 may be understood as portions corresponding to a connecting portion 314. When it is said that the handle portion 320 eccentrically extends, preferably, it may be understood that the handle portion 320 extends from a region biased to any one side of the both ends 310d from the central portion 310c of the retracting base portion 310.

Specifically, preferably, the connecting region a may be formed between any one end of the both ends 310d of the retracting base portion 310 and the central portion 310c and may be formed at a portion corresponding to a canine tooth and a premolar tooth at a left side or a right side.

That is, because the handle portion 320 is disposed to be eccentric toward the left side or the right side with respect to the midline of the inside of the oral cavity, a relatively large space into which a dental instrument or the like may be inserted is formed at the other side of the handle portion 320 inside the oral cavity. In this way, because a handling radius of the oral scanner and the dental instrument is enlarged, the convenience of task can be considerably improved. Also, because interference with the handle portion 320 is minimized during a task of handling the oral scanner and the dental instrument, convenience of task can be further improved.

Here, an outer retracting portion 312 is formed in an arch shape having a predetermined radius value corresponding to the outer portion 1b of the gum 1. Then, the handle portion 320 may extend in a direction e2 that vertically intersects an arch-shaped extending direction e1 of the outer retracting portion 312. Consequently, the handle portion 320 may extend outward in a diagonal direction from the retracting base portion 310 corresponding to a natural movement radius of both arms of the operator. In this way, because an excessive bending of a wrist is prevented when gripping the handle portion 320, a fatigue degree during the scanning can be decreased, and convenience of task can be considerably improved.

Further, a pressing support extension 321 that is gradient upward from the connecting region a may be disposed at one end 320a at which the handle portion 320 is connected to the retracting base portion 310. Here, the pressing support extension 321 may be formed to be convexly round toward an upper surface so that a finger placed above, e.g., a thumb f1, is pressed and supported when the handle portion 320 is gripped. Also, the grip portion 322 may be connected outward from the pressing support extension 321 and have a support groove portion 322a that is concave toward a lower surface so that a finger placed below, e.g., a forefinger f2, is seated and supported when the handle portion 320 is gripped. Here, preferably, the support groove portion 322a may be understood as an opposite surface (lower surface) of the pressing support extension 321 that protrudes to be substantially convex upward.

Further, when the handle portion 320 is gripped, the support groove portion 322a concavely formed at the lower surface of the grip portion 322 is seated and supported at the upper surface side of the forefinger f2. Simultaneously, as the thumb f1 is pressed and supported at the upper surface of the pressing support extension 321 that protrudes convexly at an opposite surface of the support groove portion 322a, the handle portion 320 may be firmly clamped and fixed between the fingers f1 and f2. Consequently, because movement or a position change of a dental tractor 300 is minimized while the operator grips the handle portion 320, a state in which the soft tissues are retracted and held can be stably maintained. In this way, a scanned image can be promptly and clearly acquired in the state in which the soft tissues are retracted and held, and reliability of the acquired image can be improved.

When the convexly protruding upper surface of the pressing support extension 321 is pressed and supported by the thumb f1 in a state in which the support groove portion 322a is seated and supported at the forefinger f2, the retracting base portion 310 may be stably pressed toward the inside of the oral cavity of the person to be treated due to the leverage effect. In this way, because soft tissues of gum whose image is desired to be scanned may be easily retracted with only a minimal pressing force when the dental retractor 300 is gripped, convenience of operation can be considerably improved. Further, because a pressing force applied during handing of the operator is intensively applied to the retracting base portion 310 as the pressing support extension 321 protrudes convexly toward the upper surface, retraction stability using the dental retractor 300 can be further improved.

A support guide surface 323 expanding in both directions and having a predetermined area to be adhered to and supported at a palm of the operator when the handle portion 320 is gripped may be further formed at an end of the grip portion 322. Consequently, because the handle portion 320 substantially has a shape that naturally corresponds to a profile of a fisted hand when gripped, a grip feeling can be considerably improved. Because a state in which the handle portion 320 is gripped is more stably maintained, the position of the retracting base portion 310 may be firmly fixed.

According to circumstances, an embossed non-slip portion (not illustrated) may be further formed at the pressing support extension 321, the support groove portion 322a, and the support guide surface 323 to prevent fingers and a palm from sliding when the handle portion 320 is gripped.

FIG. 6 is a plan view of a dental retractor according to a fourth embodiment of the present invention. In the present embodiment, because fundamental configurations except holding portions 416 and holding groove portions 426 are the same as in the above-described third embodiment, detailed descriptions of overlapping configurations will be omitted.

As illustrated in FIG. 6, a handle portion 420 may be configured to be selectively attached to or detached from a retracting base portion 410. For this, the holding portions 416 and the holding groove portions 426 to which the holding portions 416 are fitted may be respectively formed at one end of the handle portion 420 and a side of an outer retracting portion 412 facing the one end. Here, one or more non-continuous alignment portions may be formed at the holding portions 416 and the holding groove portions 426 to prevent rotation and movement in a state in which the holding portions 416 and the holding groove portions 426 are fitted to and engaged with each other.

Specifically, the holding portions 416 may be symmetrically disposed at both sides with respect to a central portion of the outer retracting portion 412. The holding groove protrusions 426 may be formed in the shape of a groove to which an outer surface of the holding portion 416 is fitted. Accordingly, after the handle portion 420 is separated, the handle portion 420 can be operated by the operator's right hand or left hand just by fitting the handle portion 420 into the holding portion 416 formed at one side or the other side of the outer retracting portion 412. In this way, because a limitation of a gripping direction is minimized even when the handle portion 420 eccentrically extends from a central portion of the retracting base portion 410, usability can be considerably improved.

Here, because rotation or movement is limited by outer surface and inner surface profiles of the holding portion 416 and the holding groove portion 426 and the non-continuous alignment portions formed as steps that non-continuously extend, the engaging angle and position of the handle portion 420 may be fixed. Here, the holding portion 416 and the holding groove portion 426 may be formed in a polygonal shape in which continuing directions of each surface is different, and according to circumstances, the holding portion 416 and the holding groove portion 426 may be formed as D-cut portions or as separate protrusions/grooves. Further, the holding portions may be symmetrically formed partially at both sides of the outer retracting portion or may be formed at an entire region of a central portion and both sides of the outer retracting portion, and the holding portion may be formed at one end of the handle portion. According to circumstances, a holding member in the shape of forceps or a clamp may be disposed at one end of the handle portion, and the handle portion may be clamped and fixed to the retracting base portion by the holding member.

FIG. 7 is a plan view of a dental retractor according to a fifth embodiment of the present invention, FIG. 8 is an exemplary view illustrating an inside of an oral cavity in which the dental retractor according to the fifth embodiment of the present invention is installed, and FIG. 9 is an exemplary view illustrating a state in which the inside of the oral cavity in which the dental retractor according to the fifth embodiment of the present invention is installed is scanned. In the present embodiment, because fundamental configurations except a retracting base portion 510 are the same as in the above-described third embodiment, detailed descriptions of overlapping configurations will be omitted. Here, preferably, an upper end of a gum 4 which will be described below may be understood as an alveolar portion in which a natural tooth or an artificial tooth are substantially placed. Further, preferably, the gum 4 in the present embodiment may be understood as an upper jaw, substantially.

As illustrated in FIGS. 7 to 9, a retracting base portion 510 may be inserted between the outer portion 4a of the gum 4 and an inner surface of lips 5 so that the soft tissues are retracted and held outward. When the retracting base portion 510 is pressed toward a lower end 4c of the gum 4 while being inserted, the soft tissues may be separated from the outer portion 4a of the gum 4 corresponding to a thickness of the retracting base portion 510, and the soft tissues may be spaced apart from the outer portion 4a of the gum 4 as an external force is applied outward from the oral cavity.

That is, as an inner peripheral surface 511b of the retracting base portion 510 is spaced apart from the outer portion 4a of the gum 4, the soft tissues adhered to an outer peripheral surface 511a of the retracting base portion 510 may be spaced apart and separated from the gum 4. Accordingly, an entire outer shape of the gum 4 up to mesial and distal side thereof can be clearly exposed at a time, and accuracy of a scanned image acquired by scanning the gum 4 can be improved.

Here, the retracting base portion 510 may be a wire body that is round corresponding to an entire arch-shaped profile of the outer portion 4a from the mesial side corresponding to an anterior teeth side of the gum 4 to a distal side 4d corresponding to a molar teeth side at both sides. Consequently, when the retracting base portion 510 is inserted into the oral cavity, labial soft tissues corresponding to the anterior teeth side and distal soft tissues corresponding to the molar teeth side may be simultaneously spaced apart and separated from the outer portion 4a of the gum 4. In this way, because the entire outer shape of the gum 4 can be scanned at a time in a state in which an oral scanner s is inserted into the oral cavity of the person to be treated, convenience of task can be considerably improved. Furthermore, because a distortion between acquired scanned images can be minimized, reliability of information can be improved, and because time and a process required for correcting a distorted image can be minimized, convenience of task can be improved.

Because the retracting base portion 510 is formed as the wire body substantially having a small cross-sectional diameter, a portion occluded by the outer portion 4a of the gum 4 may be minimized by the retracting base portion 510 while the soft tissues are firmly retracted. Accordingly, because the outer portion 4a of the gum 4, that is, a substantial outer surface of a maxillary process, is entirely exposed, a scanning area through the oral scanner s may be maximally secured. In this way, an amount of information that can be provided from an acquired scanned image can be maximally calculated, and reliability of information can also be considerably improved.

Here, an alignment reference portion 518 configured to guide an aligned arrangement corresponding to a midline inside the oral cavity may be disposed at a central portion of the retracting base portion 510.

Specifically, when the alignment reference portion 518 is disposed corresponding to the midline, the inner peripheral surface 511b of the retracting base portion 510 may be disposed to be spaced apart from the entire outer portion 4a of the gum 4 by an equal interval. In this way, because the outer portion 4a of the gum 4 is entirely exposed and thus the scanning area is maximally secured, precision and reliability of the scanned image can be considerably improved. Because an outer surface of the retracting base portion 510 is scanned together with the gum 4, image information in a state in which the alignment reference portion 518 is disposed corresponding to the midline may be included in the scanned image. Consequently, even in a case in which a midline inside the oral cavity is difficult to be calculated as in a person to be treated who is edentulous or partially edentulous, information on the midline can be easily calculated on the basis of an image of the alignment reference portion 518 included in the scanned image.

Here, the alignment reference portion 518 may be disposed to be aligned corresponding to a labial frenulum 5a.

Specifically, the labial frenulum 5a, which is a crease tissue that connects the outer portion 4a of the gum 4 and the inner surface of the lips 5, is formed along the midline, and limits a movement range of the lips 5 is formed at the lower end 4c of the gum 4. That is, the alignment reference portion 518 may be disposed to be aligned with respect to the labial frenulum 5a even in a case of a person to be treated who is edentulous or partially edentulous. Consequently, because accurate midline position information is calculated from a scanned image acquired by scanning the inside of the oral cavity in which a dental retractor 500 is installed, precision of an implant placement plan established on the basis of the midline position information can be considerably improved.

Here, the alignment reference portion 518 may be formed by one surface of the retracting base portion 510 corresponding to the lower end 4c of the gum 4 being concavely recessed.

Specifically, when the retracting base portion 510 is inserted between the outer portion 4a of the gum 4, the inner surface of the lips 5, and an inner surface 5b of cheeks, the retracting base portion 510 is disposed so that the one surface corresponds to the lower end 4c of the gum 4. Here, the retracting base portion 510 can be accurately disposed to be aligned corresponding to the midline just by a simple method in which the labial frenulum 5a is inserted into a concave inner space 518b of the alignment reference portion 518.

That is, the retracting base portion 510 may be easily and accurately aligned corresponding to the midline inside the oral cavity with respect to the labial frenulum 5a. When the retracting base portion 510 is pressed toward the lower end 4c of the gum 4, the inner peripheral surface 511b of the retracting base portion 510 is spaced apart from the outer portion 4a of the gum 4. In this way, soft tissues at the inner surface of the lips 5 and the inner surface 5b of the cheeks may be spaced apart from the outer portion 4a of the gum 4, and the gum 4 may be entirely exposed. Further, because left-right movement of the retracting base portion 510 may be held in a state in which the labial frenulum 5a is inserted into the inner space 518b of the alignment reference portion 518, the position of the retracting base portion 510 can be substantially fixed without a separate fixer during the scanning task.

Alternatively, when remaining teeth at the anterior teeth side are present in the gum 4 of the person to be treated, the alignment reference portion 518 may be disposed corresponding to a teeth arrangement surface between a pair of anterior teeth corresponding to the midline. Here, as a protrusion 518c that is convex toward the other surface of the alignment reference portion 518 is disposed to be aligned to the teeth arrangement surface between the pair of anterior teeth, the retracting base portion 510 may be accurately disposed corresponding to the midline.

Further, a reference indicating portion 518a may be further included to surround in a circumferential direction of an outer peripheral surface at a central portion of the alignment reference portion 518. That is, even when profiles of the concave inner surface 518b at the one surface and the protrusion 518c at the other surface of the alignment reference portion 518 are gently formed, the reference indicating portion 518a may be utilized as a clear reference index for the midline.

According to circumstances, the alignment reference portion may be formed by the one surface of the retracting base portion protruding convexly or may be marked just by the reference indicating portion at the central portion of the retracting base portion. Further, the alignment reference portion may be formed in the shape of a concave groove or a convex protrusion as a whole in the circumferential direction at the central portion of the retracting base portion. The reference indicating portion may be formed in the shape of an arrow that narrows in a direction toward the one surface or the other surface of the retracting base portion and may be formed with various indicators that may be a clear reference index.

A variable holding portion 517 in which a cross-sectional transverse width d3 gradually becomes narrower than a cross-sectional longitudinal width d2 toward a tip 517a may be integrally formed with both ends of the retracting base portion 510. Here, the variable holding portion 517 may be selectively deformed due to an external force corresponding to profiles of both ends of the gum 4 extending in an arch shape. Here, when it is said that the shape of the variable holding portion 517 is deformed, preferably, it may be understood that an interval between a pair of variable holding portions 517 at the both ends of the retracting base portion 510, and an extension angle with the central portion, a curvature, or the like of the retracting base portion 510 are deformed due to an external force.

Consequently, the interval between the inner peripheral surface 511b of the retracting base portion 510 and the outer portion 4a of the gum 4 may be elastically adjusted corresponding to various profiles of the gum 4 according to individual variations of people to be treated.

Here, the central portion of the retracting base portion 510 is disposed so that the cross-sectional longitudinal width d2 and a cross-sectional transverse width d1 substantially correspond. Consequently, because an arbitrary deformation of the retracting base portion 510 is prevented even when an external force is applied toward the retracting base portion 510 in a state in which a handle portion 520 is gripped by the operator, a state in which the soft tissues are retracted may be firmly supported. The variable holding portion 517 may be formed to have a substantially elliptical cross-section because the variable holding portion 517 is formed so that the cross-sectional transverse width d3 gradually narrows toward the tip 517a. Consequently, the variable holding portion 517 may be easily inserted into a narrow gap at which the outer portion 4a of the gum 4 and the inner surface of the lips 5 are adhered. Because the tip 517a of the variable holding portion 517 is formed to be relatively thin, a feeling of irritation can be minimized when the dental retractor 500 is inserted into the oral cavity, and discomfort of the person to be treated can be considerably decreased. Here, the cross-sectional longitudinal width d2 is formed to substantially correspond to the cross-sectional longitudinal width d2 at the central portion of the retracting base portion 510 while the cross-sectional transverse width d3 narrows toward the tip 517a of the variable holding portion 517. Accordingly, the separation interval between the outer portion 4a of the gum 4 and the soft tissues at the inner surface 5b of the cheeks can be maximized while an outer area that retracts and holds the soft tissues at the inner surface 5b of the cheeks is maintained.

Here, the retracting base portion 510 may include a soft wire portion 510a whose shape is maintained in a three-dimensionally plastically deformed state corresponding to the profile of the outer portion 4a of the gum 4 due to an external force and an outer skin portion 510b formed of a synthetic resin material that surrounds an outside of the wire portion 510a. That is, when it is said that the cross-sectional transverse width d3 at the tip of the variable holding portion 517 is narrower than the cross-sectional longitudinal width d2, preferably, it may be understood that the cross-sectional transverse width d3 of both ends of the wire portion 510a is formed in an elliptical shape that is narrower than the cross-sectional longitudinal width d2. Here, because the wire portion 510a and the outer skin portion 510a correspond to the wire portion 10a (see FIG. 1) and the outer skin portion 10b (see FIG. 1) of the first embodiment, detailed descriptions on materials and functions thereof will be omitted.

Further, the tip 517a of the variable holding portion 517 may be formed to have a round outer surface. Consequently, as the tip 517a of the variable holding portion 517 is smoothly inserted between the outer portion 4a of the gum 4 and the inner surface of the lips 5 which are adhered to each other, an occurrence of pain or wound due to the soft tissues inside the oral cavity being scratched or pricked may be prevented.

A retracting extension bent to be inclined toward the other surface of the retracting base portion 510 may be further included at the tip 517a of the variable holding portion 517. That is, buccal soft tissues, particularly, soft tissues at the molar teeth side in which a distribution amount of soft tissues is relatively higher compared to the labial side may be pressed and retracted further toward the inside of the oral cavity from the lower end 4c of the gum 4 by the retracting extension. Consequently, because the entire outer shape of the gum 4 including the buccal and retromolar trigone outer portions as well as the labial outer portion is clearly exposed, precision and accuracy of the scanned image can be further improved.

Here, an outer surface of the palate 6 that continues from the inner portion 4b of the gum 4 may be clearly exposed while the lips 5 at the maxillary side and the soft tissues of the lips 5 and the inner surface 5b of the cheeks are retracted to be spaced apart from the outer portion 4a of the gum 4. Consequently, an entire outer shape of the upper jaw may be precisely acquired even during manufacture of an implant in which information on an outer shape of the palate 6 is required as when designing and manufacturing maxillary dentures. In this way, because a manufactured implant and the inside of the oral cavity of the person to be treated can be fitted better, reliability of masticatory efficiency and satisfaction with use of the person to be treated can be considerably improved.

A variable support extension 521 that is selectively deformed in a convex shape toward the other side surface of the handle portion 520 may be included at one end of the handle portion 520 so that the variable support extension 521 is pressed and supported by a finger placed at the other surface of the handle portion 520 when the handle portion 520 is gripped by the operator. Here, preferably, the variable support extension 521 may be understood as a portion corresponding to the pressing support extension 321 (see FIG. 5) of the third embodiment described above.

That is, when the retracting base portion 510 is inserted between the outer portion 4a of the gum 4 and the inner surface of the lips 5 in the state in which the handle portion 520 is gripped by the operator, one surface of the variable support extension 521 is disposed at an outer surface of the lips 5 of the person to be treated. Consequently, when a convex outer surface at the other surface of the variable support extension 521 is pressed by the thumb in a state in which one surface of the variable support extension 521 is seated at the forefinger, the retracting base portion 510 installed inside the oral cavity may be pressed toward the lower end 4c of the gum 4. Also, when a retraction force of retracting outward from the oral cavity is applied, the outer portion 4a of the gum 4 and the inner surface of the lips 5 may be spaced apart.

Because the lips 5 are retracted outward from the oral cavity as the one surface of the variable support extension 521 is disposed to be adhered to the lips 5, the outer portion 4a of the gum 4 may be more clearly exposed. Further, because movement of the lips 5 is prevented even when unconscious movement of the person to be operated occurs, interference with the lips 5 is prevented during movement of the oral scanner s, and reliability of a scanned image acquired by scanning can be considerably improved.

FIG. 10 is a plan view of a dental retractor according to a sixth embodiment of the present invention. In the present embodiment, because fundamental configurations except an inner retracting portion 612 are the same as in the above-described fifth embodiment, detailed descriptions of overlapping configurations will be omitted.

As illustrated in FIG. 10, an arch-shaped inner retracting portion 612 corresponding to a profile of the inner portion of the gum 4 may be further included in a retracting base portion 610. Here, both ends of the inner retracting portion 612 may be selectively engaged with both ends of the retracting base portion 610.

Specifically, the inner retracting portion 612 may be formed to have an inner peripheral surface corresponding to the inner portion of the gum 4 and a pressing holding portion 615 in which the tongue is accommodated and held formed at a concave outer peripheral surface. An extending connecting portion 614 that surrounds a distal outer portion of the gum 4 and has an engaging portion 612d selectively engaged with the retracting base portion 610 may be formed at both ends of the inner retracting portion 612.

When the inner retracting portion 612 is engaged with the retracting base portion 610, the tongue may be accommodated and held in the pressing holding portion 615. As the retracting base portion 610, the inner retracting portion 612, and the extending connecting portion 614 are entirely connected, an accommodating space in which the entire outer surface of the gum 4 is accommodated may be formed. That is, as the inner retracting portion 612 is selectively engaged, the tongue adjacent to the inner portion of the gum as well as the soft tissues adjacent to the outer portion of the gum 4 may be simultaneously held. Consequently, because a single dental retractor can be elastically applied to the upper jaw or the lower jaw just by a simple operation of attaching or detaching the inner retracting portion 612, convenience in use and economic feasibility can be considerably improved.

Here, the retracting base portion 610 and an engaging portion 611d and the engaging portion 612d respectively formed at both ends of the inner retracting portion 612 may be formed in a structure in which a protrusion formed at one side is inserted into a groove formed at the opposite side. Here, preferably, the both ends of the inner retracting portion 612 may be understood as a tip of the extension connecting portion 614.

Further, the both ends of the inner retracting portion 612 may be engaged to be disposed at the lower end of the gum 4 while the retracting base portion 610 and the both ends of the inner retracting portion 612 overlap each other. Consequently, an external force applied so that the retracting base portion 610 is pressed toward the lower end of the gum 4 may be transmitted to press the both ends of the inner retracting portion 612. In this way, as the both ends of the inner retracting portion 612 are clamped and fixed between the lower end of the gum 4 and the both ends of the retracting base portion 610, an arbitrary separation of the inner retracting portion 612 during the scanning task can be prevented.

The dental retractors 100, 200, 300, 400, 500, and 600 can be widely used for various dental treatments such as various implant placements and orthodontic treatments that require a clear scanned image of an inside of an oral cavity as well as for planning an implant placement. Further, the dental retractors 100, 200, 300, 400, 500, and 600 may also be used to retract and hold soft tissues such as the tongue and the lips even during treatment of periodontal diseases in addition to a task of scanning an inside of an oral cavity.

INDUSTRIAL APPLICABILITY

The present invention is applicable to a manufacturing industry of dental implant products.

The invention claimed is:

1. A dental retractor comprising:
a retracting base portion that includes an inner retracting portion extending in an arch-shaped profile and configured to surround and face an inner portion of a gum of a patient at any one side of an upper jaw and a lower jaw inside an oral cavity of the patient and having a pressing holding portion formed at an outer peripheral surface thereof so that a tongue of the patient is capable of being accommodated therein, and an outer retracting portion integrally extending from the inner retracting portion and extending in an arch-shaped profile and configured to surround and face an outer portion of the gum; and
a handle portion including a grip portion connected to and extending outward from the retracting base portion,
wherein the inner retracting portion and the outer retracting portion are continuous with each other such that the inner retracting portion and the outer retracting portion together form a closed curved shape which defines a single opening therein,
wherein the single opening is formed completely through the retracting base portion such that the inner portion of the gum and the outer portion of the gum can together pass through the retracting base portion via the single opening when the retracting base portion is inserted into the oral cavity allowing the gum to be positioned inside the single opening, wherein the single opening includes a predetermined first interval and a predetermined second interval, wherein an inner peripheral surface of the inner retracting portion is configured to be spaced apart from the inner portion of the gum by the predetermined first interval, and wherein an inner peripheral surface of the outer retracting portion is configured to be spaced apart from the outer portion of the gum by the predetermined second interval so that the inner portion of the gum and the outer portion of the gum are exposed and soft tissue within the oral cavity is substantially spaced apart from the gum of the patient; and
wherein the inner retracting portion and the outer retracting portion comprise a soft wire forming the closed curved shape and configured to maintain a three-dimensional plastically deformed shape due to application of an external force, and an outer skin configured to surround an outside of the soft wire.

2. The dental retractor of claim 1, wherein:
the handle portion is connected to an outer end of the retracting base portion such that the outer end of the retracting base portion and an end of the grip portion are connected by an extending bent portion which is inclined upward, and wherein the inner retracting portion and the outer retracting portion are integrally connected by a connecting portion that is round outward; and
wherein the connecting portion is bent upward to face an outer surface of the extending bent portion so that an end portion of the connecting portion is configured to support a state in which upper and lower jaws are spaced apart.

3. The dental retractor of claim 1, further comprising an extending bent portion including a pair of bent portions which are spaced a predetermined interval from each other at an outer end of the outer retracting portion configured to retract lips of the patient outward,
wherein the grip portion is formed so that ends extending from the pair of extending bent portions are adjacent to each other; and
wherein the handle portion further includes: a pressing support portion which connects opposite sides of the grip portion by a predetermined width, and is configured to support fingers during gripping.

4. The dental retractor of claim 1, wherein the handle portion extends from a connecting region formed on the outer retracting portion and spaced apart from a central portion of the retracting base portion and arranged on either a left side or a right side of the outer retracting portion, and the grip portion is connected to the retracting base portion by a stepped portion which extends downwardly from the grip portion and extends upwardly from the retracting base portion.

5. The dental retractor of claim 4, wherein the handle portion extends outward in a diagonal direction from the connecting region and perpendicularly from the outer retracting portion.

6. The dental retractor of claim 4, further comprising, at an end of the grip portion, a support guide surface expanding in a widthwise direction and having a portion configured to be supported with a palm of a hand when the handle portion is gripped by the hand,
wherein, to allow the handle portion to be selectively attached to or detached from the retracting base portion, a holding portion including one or more non-continuous alignment portions is formed at an end of handle portion opposite to the end of the grip portion and a holding groove portion to which the holding portion is fitted is formed at a side of the outer retracting portion facing the end of handle portion.

* * * * *